United States Patent
McBride

(10) Patent No.: US 8,226,656 B2
(45) Date of Patent: Jul. 24, 2012

(54) MINIMALLY INVASIVE SYSTEMS AND METHODS FOR INSERTION OF A CONNECTING MEMBER ADJACENT THE SPINAL COLUMN

(75) Inventor: Larry McBride, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1081 days.

(21) Appl. No.: 12/104,231

(22) Filed: Apr. 16, 2008

(65) Prior Publication Data

US 2009/0264930 A1 Oct. 22, 2009

(51) Int. Cl.
*A61B 17/70* (2006.01)

(52) U.S. Cl. ............... 606/86 A; 606/250; 606/914

(58) Field of Classification Search .......... 606/246–278, 606/86 A

See application file for complete search history.

(56) References Cited

U.S. PATENT DOCUMENTS

| | | | |
|---|---|---|---|
| 4,448,191 A | 5/1984 | Rodnyansky et al. | |
| 5,242,443 A | 9/1993 | Kambin | |
| 6,821,277 B2 | 11/2004 | Teitelbaum | |
| 2004/0039384 A1 | 2/2004 | Boehm, Jr. et al. | |
| 2004/0138662 A1 | 7/2004 | Landry et al. | |
| 2004/0143265 A1* | 7/2004 | Landry et al. | 606/61 |
| 2004/0215190 A1 | 10/2004 | Nguyen et al. | |
| 2005/0033299 A1 | 2/2005 | Shluzas | |
| 2005/0080418 A1* | 4/2005 | Simonson et al. | 606/61 |
| 2005/0085813 A1 | 4/2005 | Spitler et al. | |
| 2005/0131408 A1 | 6/2005 | Sicvol et al. | |
| 2005/0131421 A1 | 6/2005 | Anderson et al. | |
| 2005/0131422 A1 | 6/2005 | Anderson et al. | |
| 2005/0154389 A1 | 7/2005 | Selover et al. | |
| 2005/0192570 A1 | 9/2005 | Jackson | |
| 2005/0192589 A1* | 9/2005 | Raymond et al. | 606/99 |
| 2005/0228380 A1 | 10/2005 | Moore et al. | |
| 2005/0251139 A1 | 11/2005 | Roh | |
| 2005/0277934 A1 | 12/2005 | Vardiman | |
| 2006/0111712 A1 | 5/2006 | Jackson | |
| 2006/0111713 A1 | 5/2006 | Jackson | |
| 2006/0173454 A1 | 8/2006 | Spitler et al. | |
| 2006/0217719 A1* | 9/2006 | Albert et al. | 606/61 |
| 2006/0241600 A1 | 10/2006 | Ensign et al. | |
| 2006/0247630 A1 | 11/2006 | Lott et al. | |
| 2006/0264942 A1 | 11/2006 | Lim et al. | |

(Continued)

FOREIGN PATENT DOCUMENTS

WO    2005076868 A2    8/2005

OTHER PUBLICATIONS

European Office Action for Application No. 09158091.0 mailed Apr. 13, 2010.

*Primary Examiner* — Eduardo C Robert
*Assistant Examiner* — James Palmer

(57) ABSTRACT

A spinal surgical system includes at least one extender mounted to an anchor engaged to the spinal column. The extender extends proximally away from the anchor to a proximal end outside the patient. The extender is configured to receive a connecting member from an approach that is generally parallel or along the longitudinal axis of the extender so that the connecting member can be positioned from the proximal end of the extender to the anchor at the distal end of the extender without requiring an additional incision or puncture to accommodate the connecting member insertion.

16 Claims, 5 Drawing Sheets

U.S. PATENT DOCUMENTS

| | | |
|---|---|---|
| 2007/0049931 A1 | 3/2007 | Justis et al. |
| 2007/0073294 A1 | 3/2007 | Chin et al. |
| 2007/0078460 A1 | 4/2007 | Frigg et al. |
| 2007/0083210 A1 | 4/2007 | Hestad et al. |
| 2007/0162007 A1 | 7/2007 | Shoham |
| 2007/0173831 A1 | 7/2007 | Abdou |
| 2007/0191836 A1* | 8/2007 | Justis .................. 606/61 |
| 2007/0213714 A1 | 9/2007 | Justis |
| 2007/0233097 A1 | 10/2007 | Anderson et al. |
| 2007/0239159 A1 | 10/2007 | Altarac et al. |
| 2007/0270819 A1 | 11/2007 | Justis et al. |
| 2007/0270842 A1 | 11/2007 | Bankoski et al. |
| 2008/0015582 A1 | 1/2008 | DiPoto et al. |
| 2008/0045956 A1 | 2/2008 | Songer et al. |
| 2008/0045957 A1 | 2/2008 | Landry et al. |
| 2008/0077138 A1* | 3/2008 | Cohen et al. ............ 606/61 |
| 2008/0221626 A1* | 9/2008 | Butters et al. .......... 606/86 A |

\* cited by examiner

MINIMALLY INVASIVE SYSTEMS AND METHODS FOR INSERTION OF A CONNECTING MEMBER ADJACENT THE SPINAL COLUMN

BACKGROUND

Orthopedic devices such as spinal rods, plates, tethers, staples and other devices can be secured along the spinal column between one or more vertebral levels to stabilize the one or more vertebral levels. While surgical procedures along the spinal column for placement of such devices are becoming less invasive, there remains a need for additional improvements. The decrease in space available in the approach to the surgical site and at the surgical site for handling and manipulating of the devices increases the difficulty in maneuvering, maintaining and finally positioning of the devices during the procedure. Furthermore, the small and intricate parts commonly associated with such orthopedic devices can increase the difficulty of the installation procedure. Accordingly, systems and devices which facilitate placement of orthopedic devices along the spinal column while minimizing impact to tissue and other structures along the spinal column are desirable.

SUMMARY

Systems, methods and devices for positioning connecting member adjacent the spinal column between two or more anchors are provided. The systems include at least one extender mounted to an anchor engaged to the spinal column. The extender extends proximally away from the anchor to a proximal end outside the patient. The extender is configured to receive a connecting member from an approach that is generally parallel or along the longitudinal axis of the extender so that the connecting member can be positioned from the proximal end of the extender to the anchor at the distal end of the extender without requiring an additional incision or puncture to accommodate the connecting member insertion.

In another aspect, the systems include an extender engageable to the anchor and a retractor positionable through the extender with a distal retracting member that is pivotal from a first orientation extending along the axis of the extender to a second orientation where the retracting member extends transversely from the extender. The retracting member projects outwardly from the extender in the second orientation to retract tissue adjacent the extender in a direction away from the spinal column to allow passage of a connecting member from a distal end of the extender along a distal side of the retracting member.

In another aspect, extenders are also provided that include an inner member extending between a proximal end outside the patient and a distal end mounted to an anchor in the patient. The inner member defines a first passage extending axially therethrough to provide access to the anchor. The extenders also include an outer member around the inner member. The inner and outer members form a second passage therebetween and along the inner and outer members. The second passage allows insertion of an elongated connecting member therethrough from the proximal end of the extender to the anchor at the distal end of the extender while the first passage remains unobstructed by the connecting member.

Another aspect provides methods for positioning a connecting member along the spinal column for engagement with anchors in minimally invasive surgical procedures.

DESCRIPTION OF THE ILLUSTRATED EMBODIMENTS

Figure 1:
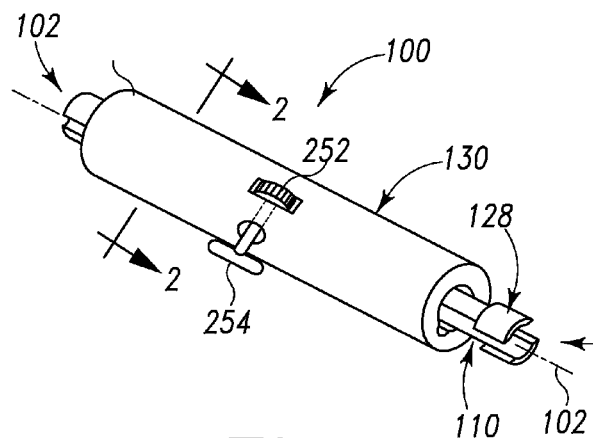
FIG. 1 is a diagrammatic perspective view of an extender for positioning a connecting member along the spinal column in a minimally invasive procedure.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

A system for positioning a connecting member adjacent the spinal column in a minimally invasive surgical procedure includes at least one extender that is engaged to the spinal column with an anchor at the distal end of the extender. The extender includes an inner member that defines a passage extending from a proximal end of the inner member to a distal end so that the passage opens into a receiver of the anchor. The extender also includes an outer member around the inner member. The outer member includes a distal end adjacent the anchor and a proximal end adjacent the proximal end of the inner member. The outer member and inner member define a second passage therebetween. A connecting member is placed inside the second passage with the connecting member oriented along the length of the extender. The second passage guides the connecting member axially along the extender to the receiver of the anchor. The leading end of the connecting member passes through or adjacent the receiver of the anchor and exits the extender or receiver in a transverse orientation to the trailing end of the connecting member is moved further axially along the extender toward the receiver of the anchor. The connecting member includes a length sized to extend to a second anchor engaged to the spinal column so that when the trailing end is located in the first anchor and the leading end is located in the second anchor, the connecting member can be secured to the anchors to stabilize the vertebrae to which the anchors are engaged. The extender allows placement of the connecting member into the patient between at least two anchors without requiring an incision or puncture other than what is provided to accommodate placement of the anchors into the patient.

Figure 2:
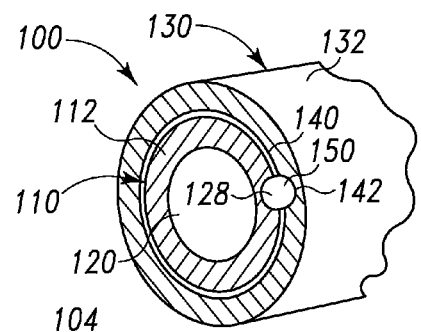
FIG. 2 is a section view along line 2-2 of FIG. 1.
Figure 3:
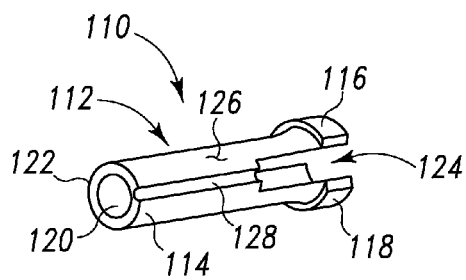
FIG. 3 is a diagrammatic perspective view of an inner member of the extender of FIG. 1.
Figure 4:
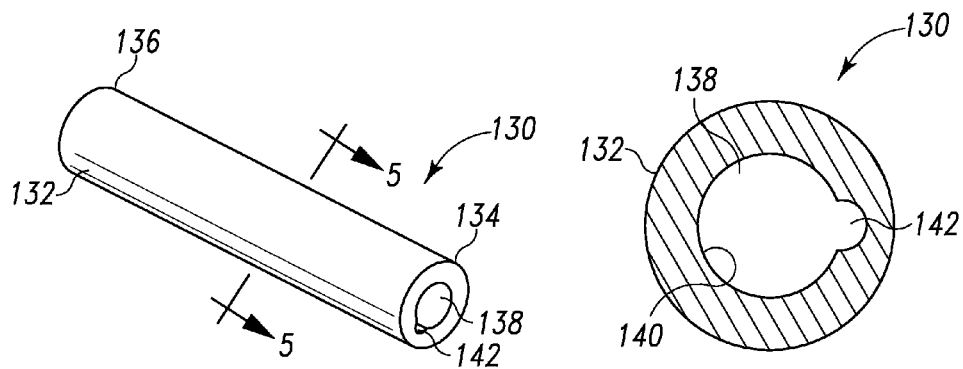
FIG. 4 is a diagrammatic perspective view of an outer member of the extender of FIG. 1.
Figure 5:
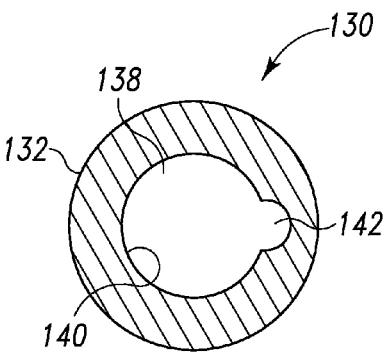
FIG. 5 is a section view along line 5-5 of FIG. 4.

In FIG. 1 there is shown one embodiment extender 100. Extender 100 includes an elongated body structure extending along a longitudinal axis 102 between a proximal end 102 and an opposite distal end 104. Extender 100 includes an inner member 110 and an outer member 130 that is positioned around inner member 110 as also shown in FIG. 2. Inner member 110 is shown in isolation in FIG. 3, and outer member 130 is shown in isolation in FIGS. 4-5.

Outer member 130 includes an elongated tubular body 132 extending along longitudinal axis 102 between a distal end 134 and an opposite proximal end 136. Body 132 includes an inner surface 140 that extends completely around and defines a central bore 138. Central bore 138 extends between and opens at distal and proximal ends 134, 136. Inner surface 140 includes a recessed portion 142 along at least one side of bore 138 that also extends between distal and proximal ends 134, 136. Recessed portion 142 forms a U-shaped groove along the length of body 132 in the illustrated embodiment. Other embodiments contemplate other shapes for recessed portion 142, including rectangular, square, polygonal, and irregular shapes. The shape of recessed portion 142 can be constant along the length of body 132 or variable along all or a portion of its length.

Inner member 110 includes an elongated body 112 extending along longitudinal axis 102. Body 112 has a tubular proximal portion 114 and a pair of arms 116, 118 extending distally from proximal portion 114. Proximal portion 114 defines a central passage 120 extending through proximal portion 114 that opens at proximal end 122. Passage 120 is also carried through between arms 116, 118 to open at a distal end of arms 116, 118. Arms 116, 118 are separated from one another with a slot 124 therebetween. Slot 124 allows arms 116, 118 to move toward one another with a force applied to an outer surface 126 of body 112 that extends along arms 116, 118. Inner member 110 also includes a recessed portion 128 extending axially along outer surface 126 of body 112 between its proximal end 122 and slot 124. Recessed portion 128 forms a U-shaped groove along the length of proximal portion 114 of body 112 in the illustrated embodiment. Other embodiments contemplate other shapes for recessed portion 128, including rectangular, square, polygonal, and irregular shapes. The shape of recessed portion 128 can be constant along the length of proximal portion 114 or variable along all or a portion of its length.

When inner member 110 and outer member 130 are assembled, recessed portions 128 and 142 are aligned with one another along proximal portion 112 of inner member 110 to define a passage 150 between inner member 110 and outer member 130, as shown in FIG. 2. When recessed portion 142 aligns with slot 124, passage 50 is formed by recessed portion 142 and slot 124. Passage 150 extends along extender 100 so that it opens adjacent distal end 102 between arms 116, 118 of inner member 112. Passage 150 defines a second passage in addition to passage 120 of inner member 110. Passage 150 allows placement of a connecting member to an anchor engaged between arms 116, 118 of inner member 110 without obstructing central passage 120, thereby leaving central passage 120 available for placement of retractors, implant inserters and drivers, and other instruments during the placement of the connecting member.

Various configurations for the connection arrangement between inner member 110 and outer member 130 are contemplated that allow the inner and outer members 110, 130 to move longitudinally relative to one another and then fix or allow adjustment in the relative longitudinal positioning therebetween while inner member 110 is engaged to an anchor. For example, in one embodiment, outer member 130 is located proximally along arms 116, 118 so that arms 116, 118 can flex apart or are otherwise spaced to receive the anchor therebetween. Outer member 130 is then movable distally relative to inner member 110 and along arms 116, 118 to compress or hold arms 116, 118 relative to one another and secure or lock the anchor between the distal ends of arms 116, 118. In another embodiment, outer member 130 is movable distally and longitudinally along inner member 110 to contact the connecting member extending outwardly from between arms 116, 118 and then reduce or position the connecting member in the anchor as the outer member and anchor are moved toward one another. Examples of suitable connecting arrangements between inner member 110 and outer member 130 can be found, for example, in U.S. Pat. No. 7,188,126; U.S. Patent App. Pub. No. 2005/0171540; U.S. Patent App. Pub. No. 2007/0049931; U.S. Patent App. Pub. No. 2007/0213714; and U.S. patent application Ser. No. 11/820,964. Each of the referenced patents, patent application publications and patent applications is incorporated herein by reference in its entirety.

Figure 6:
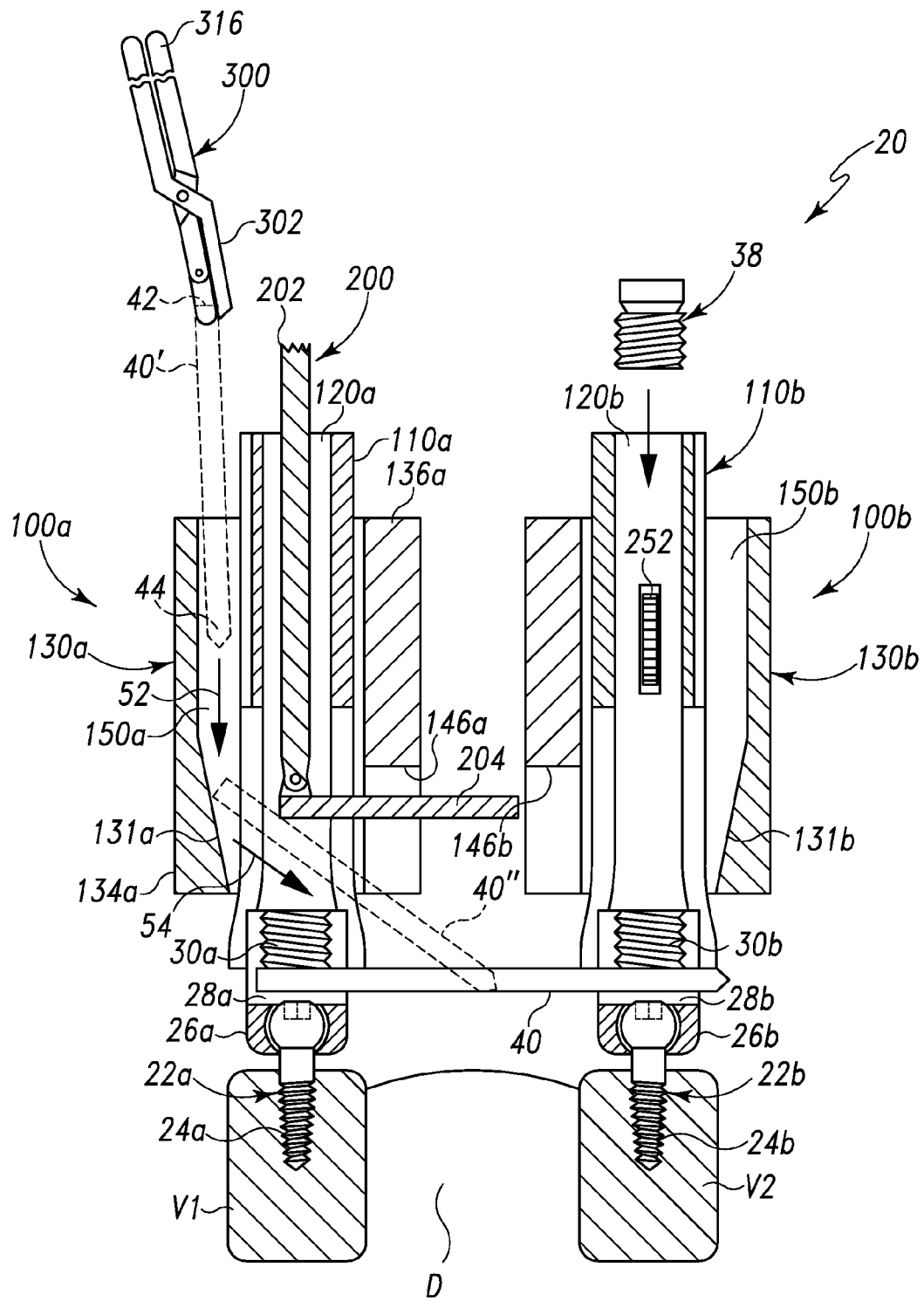
FIG. 6 is a diagrammatic sectional elevation view of a system including anchors mounted to the spinal column and extenders extending from the anchor guiding placement of a connecting member between the anchors along with a retractor and connecting member insertion instrument.

Referring now to FIG. 6, an example of a system 20 is provided that employs two extenders 100, designated as extender 100a and 100b, respectively, secured to respective ones of first and second anchors 22a, 22b. Anchors 22a, 22b are secured to respective ones of first and second vertebrae V1, V2. Disc space D is located between vertebrae V1 and V2. Although system 20 is particularly suited for minimally invasive surgical procedures, it is not restricted to such. For example, system 20 allows placement of a connecting member between anchors 20a, and 20b without requiring an incision or puncture into the patient other than what is needed to accommodate extenders 100a, 100b. However, procedures where one or more additional incisions or punctures are made not precluded. Furthermore, although its use and application is described herein with regard to spinal surgery, applications in surgeries other than spinal surgery are also contemplated.

In one form, system 20 provides at least a pair of extenders 100a, 100b mounted to anchors 22a, 22b engaged to the spinal column. Extenders 100a, 100b and anchors 22a, 22b and the components thereof are also referred to herein collectively and individually as extender or extenders 100 and anchor or anchors 22. Extenders 100a, 100b extend proximally from anchors 22a, 22b, and guide the placement of a connecting member 40 from a position remote from the spinal column and outside the patient to a position adjacent the spinal column in the patient. Extenders 100a, 100b are configured so that when connecting member 40 is adjacent the spinal column, connecting member 40 extends between at least a pair of anchors 22a, 22b. Connecting member 40 can be secured to anchors 22a, 22b with securing member 38 (only one shown) and provides stabilization of the spinal column segment to which anchors 22a, 22b are attached.

In one embodiment, each of extenders 100a, 110b includes a second passage 150a, 150b between the inner members 110a, 110b and outer members 130a, 130b thereof. In another embodiment, only one of extenders 100a, 100b is provided with second passage 150. In another embodiment, the at least a pair of extenders includes three or more extenders engaged to respective one of three or more anchors.

In one embodiment, connecting member 40 is an elongated rod and anchors 22a, 22b are bone screws. Connecting member 40 can be rigid, semi-rigid, flexible, elastic, non-compression load bearing, or other suitable form for extending between and stabilizing adjacent portions of the spinal column when secured thereto. Connecting member 40 can be linear along its length, curved along an arc along its length, or include one or more compoundly curved segments or combined curved and linear segments.

The bone screws can be multi-axial type screws with a receiver portion 24a, 24b pivotally mounted to the proximal end of a screw portion 26a, 26b. The receiver portions 24a, 24b each define a receptacle 28a, 28b that receives connecting member 40 therein when connecting member 40 is oriented to extend between anchors 22a, 22b. Receptacles 28a, 28b are located between a pair of axially extending arms of the respective anchor 22a, 22b and the arms include internal threads 30a, 30b to threadingly engage a respective securing member 38.

Examples of multi-axial screw type anchors include the CD HORIZON® M-8 and M10 Multi-Axial Screws and the screws of the CD HORIZON® LEGACY™ Spinal System, all sold by Medtronic Sofamor Danek, Inc. It should be understood, however, that other anchors are contemplated, including those that are multi-axial or uni-axial in form or function, and those that include means other than a bone screw for engaging the vertebrae, such as hooks, pins, staples, plates, interbody devices and cages, rivets, and suture anchors, for example. Furthermore, the receiver portions can include any suitable form or structure for engagement with a connecting member.

In FIG. 6, system 20 includes first extender 100a and second extender 100b. Extenders 100a, 100b are mounted to receiver portions 26a, 26b of the respective anchor 22a, 22b. Extenders 100a, 100b extend proximally from the respective anchors 22a, 22b through the tissue between the skin and the spinal column such that their proximal ends project from the skin and tissue of the patient for access by the surgeon. Extenders 100a, 100b each define a minimally invasive path for delivery of connecting member 40 through the tissue of the patient to anchors 22a, 22b engaged to vertebrae V1 and V2. The minimally invasive path reduces the tissue retraction and eliminates dissection between extenders 100a, 100b to accommodate delivery of connecting member 40 to the surgical space along the spinal column between anchors 22a, 22b.

System 20 may employ various instruments to facilitate tissue retraction and placement of the connecting member through the selected extender 100a, 100b and to the anchors 22a, 22b. For example, FIG. 6 shows a distal portion of a tissue retractor 200 positioned in passage 120 of extender 100a. Tissue retractor 200 includes an elongated shaft 202 extending axially along extender 100a and a distal retracting blade 204 that is transversely oriented to shaft 202 and extender 100a. Retractor blade 204 extends toward the other extender 100b and lifts or retracts tissue along the spinal column between anchors 100a, 100b to facilitate placement of connecting member 40 between anchors 22a, 22b as connecting member 40 is maneuvered from the distal end of extender 100a toward the other extender 100b.

Also shown in FIG. 6 is an inserter 300 that engages trailing end 42 of connecting member 40 with connecting member 40 extending axially therefrom so that leading end 44 of connecting member 40 is opposite inserter 300. In the initial insertion orientation, connecting member 40 is shown in hidden lines and designated as connecting member 40'. Leading end 44 is positioned in passage 150a of extender 100a with connecting member 40' oriented along or generally paralleling longitudinal axis 102. Connecting member 40' is guided distally as indicated by arrow 52 toward anchor 22a along passage 150 until leading end 44 contacts a ramped surface portion 131a of extender 100a. Ramped surface portion 131a slopes toward inner member 110a from a location proximal of distal end 134a to distal end 134a. Ramped surface portion 131a forces or directs leading end 44 into receptacle 28a of anchor 22a as indicated by arrow 54. As connecting member 40 is moved along ramped surface portion 131a, leading end 44 is further rotated or directed more transversely to longitudinal axis 102b and toward the second extender 110b as indicated by the orientation and positioning of connecting member 40" in FIG. 6. When trailing end 42 is positioned in or adjacent to receptacle 28a of anchor 22a, leading end 44 is located in or adjacent to receptacle 28b of anchor 22b, as indicated by connecting member 40 in FIG. 6.

Retracting blade 204 lifts the tissue between anchors 22a, 22b to facilitate passage of connecting member 40 from anchor 22a to anchor 22b without an incision between extenders 100a, 100b. Other embodiments contemplate that tissue retraction is not employed and connecting member 40 is pushed through the tissue from one anchor to the other anchor. It is also contemplated that connecting member 40 can be guided along ramped surface portion 131b of extender 100b toward anchor 22a and extender 100a. In still other embodiments, it is contemplated that one of the extenders is not provided with a passage 150 or ramped surface portion 131 since connecting member 40 can be inserted by guiding it through only one of the extenders.

To facilitate retraction of tissue with retracting blade 204 and also to provide additional space in which to maneuver connecting member 40, outer member 130a is provided with a notch 146a that extends from distal end 134a toward proximal end 136a. Second extender 100b also includes a similarly located notch 146b. Notches 146a, 146b are oriented to face one another and align with slot 124 between the arms 116, 118 of the respective inner members 110a, 110b. Notches 146a, 146b and slots 124 provide an exit location for retracting blade 204 and a longitudinal path along which to move retracting blade 204 to retract tissue when deployed from extender 100.

Notches 146a, 146b and slots 124 also provide an exit path for connecting member 40 from passage 120a and an entry path into passage 120b. Thus, connecting member 40 can be initially positioned proximally of receptacles 28a, 28b and then pushed toward receptacles 28a, 28b for engagement with anchors 22a, 22b. Alternatively, one end of connecting member 40 can be secured to one of anchors 22a, 22b, and then the other anchor 22a, 22b and the vertebra to which it is engaged is pulled proximally to locate or reduce connecting member 40 in its receptacle for engagement therewith to maintain the position of the re-aligned vertebra. In another embodiment, connecting member is initially placed in one or both of receptacles 128a, 128b and does not pass through one or both of notches 146a, 146b.

Figure 7A:
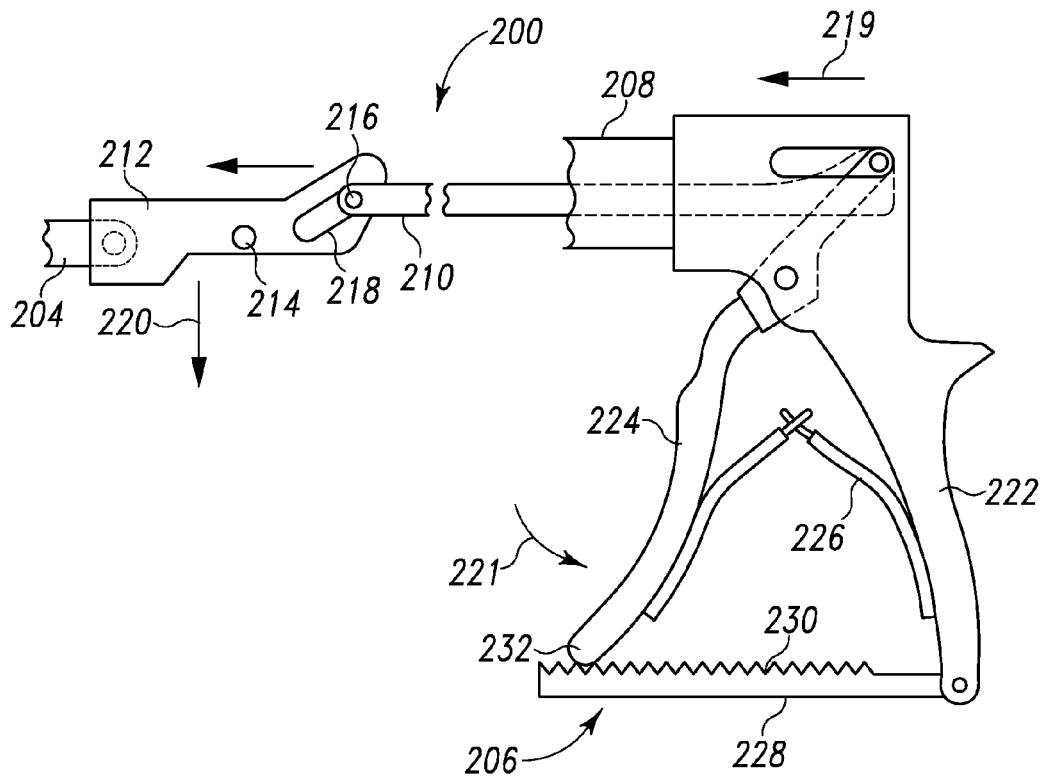
FIG. 7A is a diagrammatic elevation view of a portion of the retractor of FIG. 6 showing one embodiment handle and the connecting arrangement of the retractor blade with the handle.
Figure 7B:
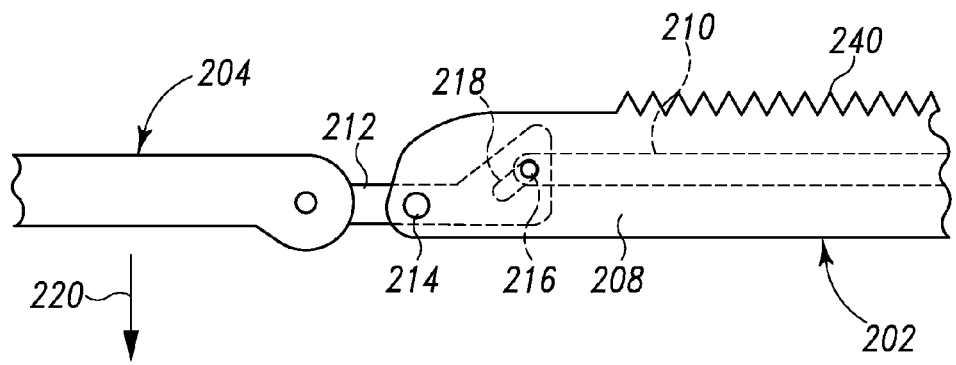
FIG. 7B is a diagrammatic elevation view of a distal portion of the retractor of FIG. 6 showing the rack member and mounting of the blade to the rack member.

FIGS. 7A and 7B show further details of one embodiment tissue retractor 200. Tissue retractor 200 includes distal retracting blade 204 pivotally coupled to a distal end of shaft 202. A handle assembly 206 is provided at the proximal end of shaft 202. Shaft 202 includes a fixed shaft member 208 and a longitudinally movable shaft member 210 that extends along and is movable relative to fixed shaft member 208. The distal end of movable shaft member 210 is pivotally coupled with a proximal end of link member 212 at an axially movable pivot 216, as shown in FIG. 7A. Link member 212 is pivotally coupled to fixed shaft 208 at an axially fixed pivot 214. Fixed pivot 214 is offset from the axis of movement of movable shaft member 210 so that distal axial displacement of shaft member 210 moves axially movable pivot 216 along slot 218 of link member 212, causing it to pivot about fixed pivot 214. This in turn pivots retracting blade 204 mounted to link 212 in the direction of arrow 220 from its axially extended position shown in FIG. 7B to its pivoted position shown in FIG. 6.

Any suitable handle assembly for axially moving movable shaft member 210 is contemplated. In the illustrated embodiment, handle assembly 206 includes a fixed, proximal handle member 222 to which fixed shaft 208 is secured. Handle assembly 206 also includes a movable handle member 224 pivotally coupled to handle member 222 at pivot axis 223. The upper end of handle member 224 is pivotally coupled with the proximal end of movable shaft 210. As handle member 224 is moved toward handle member 222 as indicated by arrow 221, movable shaft 210 axially moves along fixed shaft 208 as indicated by arrow 219 to pivot link member 212 and retracting blade 204 about fixed pivot 214 as indicated by arrow 220. A leaf spring arrangement 226 or other suitable biasing member can be provided to normally bias handle members 222, 224 away from one another and thus bias retracting blade 204 to the axially extended position of FIG. 7B where it can be inserted through passage 120 of extender 100.

When used with extender 100, retracting blade 204 is inserted through passage 120 until it is aligned with notch 146 of outer member 130. Handle member 224 is pivoted toward handle 222 to pivot retracting blade 204 so that it pivots to extend outwardly from passage 120 and through slot 124 and notch 146 of extender 100 toward the other extender. This in turn lifts the tissue between anchors 22a, 22b to create a tunnel or place through which connecting member 40 can be positioned. A lock member 228 is pivotally coupled at one end to fixed handle member 222 and includes a ratchet surface 230 to engage a tooth 232 on movable handle member 224. The engagement between tooth 232 and ratchet surface 230 maintains the position of movable handle member 224 relative to fixed handle member 222 and thus the pivoted position of retracting blade 204.

In the illustrated embodiment, fixed shaft member 208 includes a ratchet surface 240 that provides a series of teeth extending along the length thereof. Extender 100 includes a pinion 252 mounted thereto that extends into passage 120 along a side of passage 120. Pinion 252 interfaces with ratchet surface 240 when retractor 200 is positioned in passage 120 of extender 100. A thumbwheel 254 extending from pinion 252 provides a mechanical advantage and facilitates rotation of pinion 252. Pinion 252 is rotated when engaged to ratchet surface 240 to provide a mechanical advantage in placing retracting blade 204 through the tissue. Furthermore, the elevation of the pivoted retracting blade 204 shown in FIG. 6 can be raised or lowered as needed relative to extender 100 and the spinal column and then maintained in the selected position by the engagement of pinion 252 to ratchet surface 208. A locking member or device (not shown) such as a spring loaded pawl or other mechanism can be provided to engage pinion 252 and maintain it in position and prevent it from rotating once the desired position of retracting blade 204 is selected.

It is also contemplated that other instruments for positioning in passage 120 could be provided with a ratchet surface for engagement with pinion 252. For example, a set screw driver (not shown) used to secure engaging member 38 to receive portion 26a, 26b of anchors 22a, 22b can be provided with a ratchet surface along an outer surface of its shaft that is engaged by pinion 252 when positioned in passage 120.

It is also contemplated that other embodiments are provided without pinion 252. Retractor 200 is manipulated by hand with an instrument or device mounted to the proximal end of retractor 100 that maintains its positioning relative to extender 100. For example, a bracket or clamp could be secured between retractor 200 and extender 100 to maintain and/or adjust the positioning of retractor 200 in extender 100.

Figure 8:
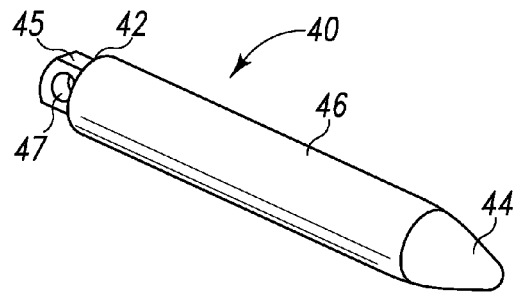
FIG. 8 is a perspective view of one embodiment connecting member.
Figure 10:
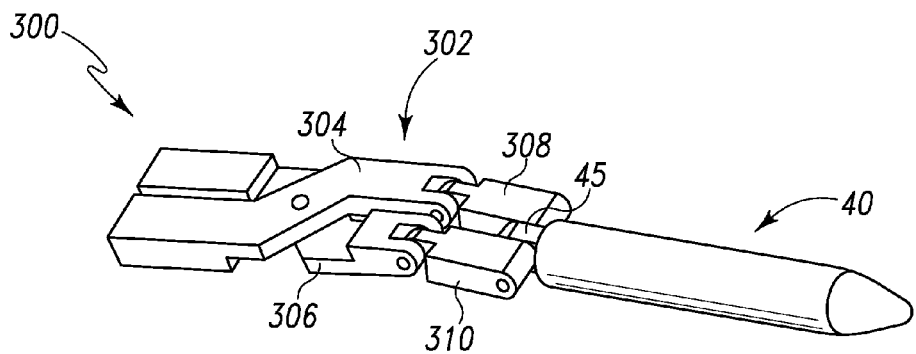
FIG. 10 is a diagrammatic perspective view showing the distal portion of the insertion instrument of FIGS. 9A and 9B engaged to the connecting member of FIG. 8.

Connecting member 40 is shown in perspective view in FIG. 8. In this embodiment, connecting member 40 includes trailing end 44 with an eyelet structure 45 extending therefrom. Eyelet structure 45 provides a flat, plate-like member with a through-bore 47 oriented transversely to the length of connecting member 40. Connecting member 40 includes an elongated cylindrical body 46 providing a rod shape extending from trailing end 44 to a tapered leading end 44. Body 46 has a uniform cross-section along its length, which can be circular as shown. However, non-uniform and/or non-circular cross-sections are also contemplated. In FIG. 10, connecting member 40 is shown connected with a distal portion of inserter 300. Inserter 300 includes a distal connecting structure 302 that is movable to engage and release eyelet structure 45 of connecting member 40.

Other embodiments contemplate various connecting member structures that extend between the anchors, including rods, wires, tethers, strands, cables, bands, plates, and struts. The connecting member may include one component, or may include two or more components. Other embodiments contemplate that the connecting member is linear, curved, a combination of linear and curved segments, a combination of linear segments angled relative to one another, or a combination of segments having differing curvatures. In one embodiment, connecting member is an elongated rod made from a metal alloy such as titanium. Other materials are also contemplated, including resorbable materials, non-resorbable material, polymers, elastomers, ceramics, other metals and metal alloys, shape memory materials, bone and bone substitute material, composites, and combinations of materials.

Figures 9A, 9B:
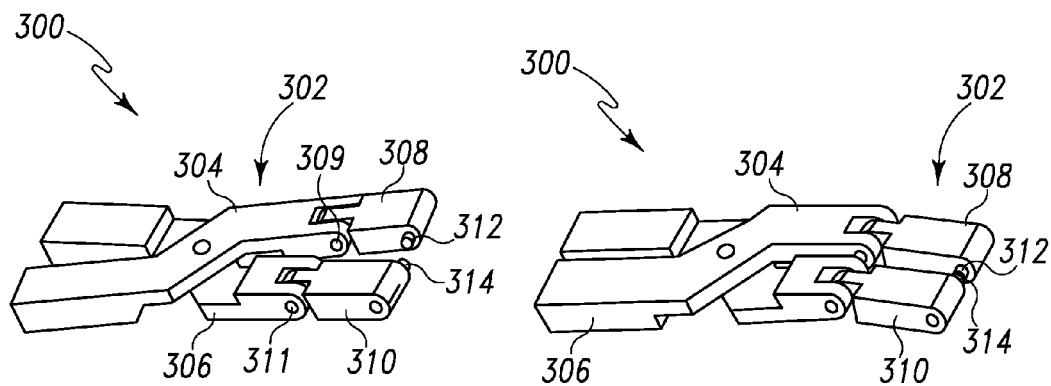
FIGS. 9A and 9B are diagrammatic perspective views of a distal portion of an insertion instrument showing a structure for engaging the connecting member.

As shown in FIGS. 9A and 9B, connecting structure 302 of inserter 300 includes a first arm 304 that is pivotally coupled to a second arm 306 in a scissors-like arrangement. The distal ends 309, 311 of arms 304, 306 include end members 308, 310 pivotally coupled thereto along pivot axes that are orthogonally oriented to the pivot axis about which arms 304, 306 pivot. Each of the end members 308, 310 includes a projecting member 312, 314 extending toward the other that are received in the through-bore 47 of eyelet structure 45 of connecting member 40, as shown in FIG. 10. Arms 304, 306 are pivoted toward and away from one another with a proximal handle structure 316 (FIG. 6) so that connecting structure can engage and release connecting member 40 therebetween. Furthermore, end members 308, 310 can pivot relative to arms 304, 306 when engaged to connecting member 40 to facilitate pivoting of connecting member 40 as its leading end rotates from the axial insertion position indicated by connecting member 40' to the final securing orientation indicated by connecting member 40 in FIG. 6.

Figure 11:
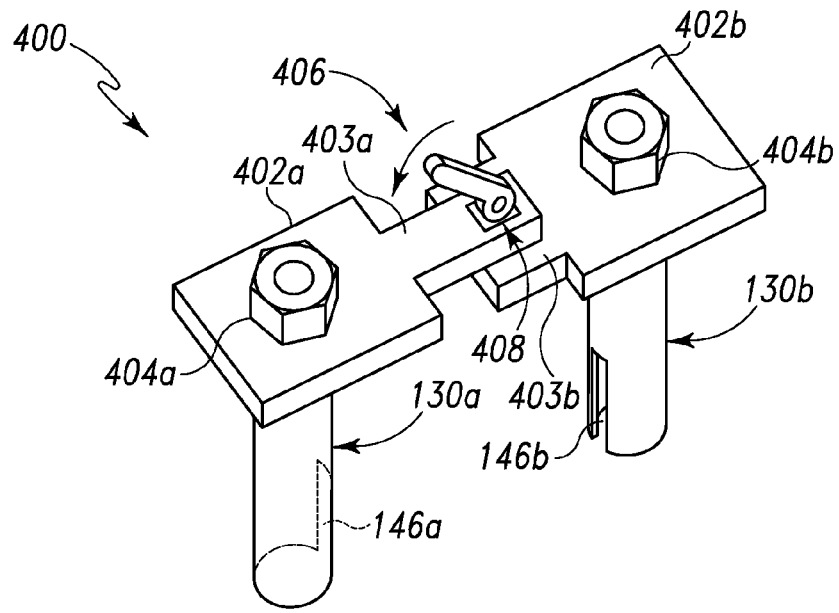
FIG. 11 is a diagrammatic view showing a pair of extenders linked to one another with an orientation guide.

FIG. 11 shows an orientation guide 400 connected between the proximal ends of extenders 100a and 100b. Orientation guide 400 includes first and second mounting members 402a, 402b that are positioned around the respective extender 100a, 100b. Mounting members 402a, 402b each define a socket 404a, 404b to receive the respective extender 100a, 100b in a fixed orientation. This fixed orientation orients and aligns notches 146a, 146b of extenders 100a, 100b toward one another to receive connecting member 40.

Figure 12A:
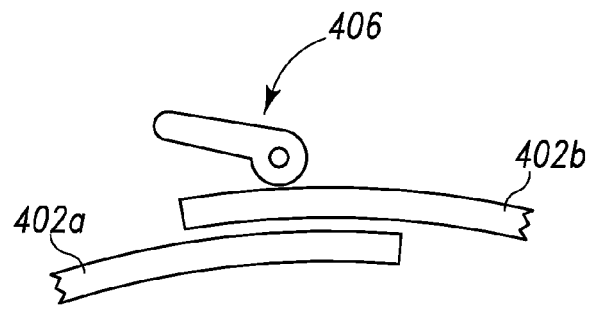
FIGS. 12A and 12B show additional embodiments in diagrammatic elevational views of a central portion of the orientation guide of FIG. 11 configured to facilitate engagement to extenders oriented in non-parallel arrangement to one another.
Figure 12B:
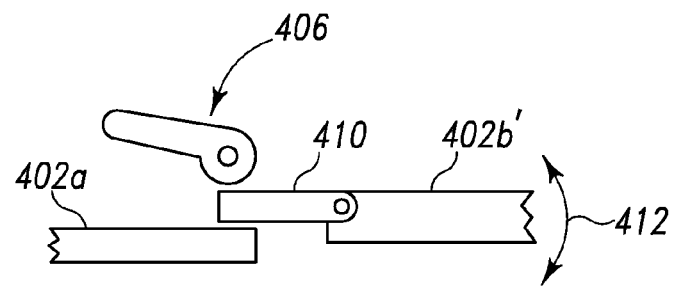

Orientation guide 400 includes a locking mechanism 406 that adjustably secures mounting members 402a, 402b relative to one another. Mounting members 402a, 402b include extensions 403a, 403b extending toward and overlapping one another in adjustable engagement with one another. Locking mechanism 406 can be a cam lock, wing nut or other suitable structure mounted to one or both of extensions 403a, 403b that maintains the relative spacing between mounting members 402a, 402b when locked, but can be loosened to allow adjustment in the relative spacing between mounting members 402a, 402b. Mounting members 402a, 402b can be coplanar as shown in FIG. 11, or angled or curved as shown in FIG. 12A to accommodate non-parallel orientations between the extenders 100a, 100b due to lordosis or kyphosis of the vertebrae or for some other reason. In another embodiment shown in FIG. 12B, one of the mounting members 402b' includes a hinged extension 410 pivotally coupled to one end thereof. Hinged extension 410 allows mounting member 402b' to pivot relative thereto and relative to mounting member 402a as indicated by arrows 412.

When positioning in the patient in a surgical procedure, each of the extenders 100 can be attached to the corresponding anchor 22 either prior to engagement of the anchor with the corresponding vertebra, as discussed above, or after the anchor has been positioned in engagement with the vertebra. For example, one embodiment of a procedure contemplates an incision over the target location of the spinal column, and that the skin and tissue are sequentially dilated to provide a minimally invasive pathway for anchor insertion and engagement to each vertebra. The respective extender 100 is then attached to the inserted anchor 22.

In another procedure, a cannulated outer needle with an inner stylet can first be inserted to the targeted region or regions of the vertebra, such as the pedicle in a posterior procedure, and aligned to provide the desired trajectory into the pedicle. Alignment can be monitored and checked with any viewing system, including radiographic, fluoroscopic, microscopic, endoscopic, loupes, naked eye, or any other suitable viewing system or instrument. After the cannulated needle and stylet are inserted into the vertebra, the inner stylet is withdrawn with the cannulated outer needle remaining engaged to the vertebra. A guidewire is positioned through the cannulated outer needle and engaged in the vertebra. The outer needle is then withdrawn so that the guidewire remains in place. The tissue around the guidewire is sequentially dilated with a number of tubular dilators of increasing diameter. When desired opening size is obtained, the guidewire and inner dilators are removed and the last inserted dilator provides a protected pathway to the pedicle or other targeted portion of the vertebra. The anchor 22 can then be positioned through the dilated pathway and engaged to the vertebra. The corresponding extender 100 is then attached to receiver portion 26 of the inserted anchor 22 as discussed above, and the dilator is removed. The procedure is then repeated to position the desired number of extenders 100, whether it is two, three or four or more extenders.

In another embodiment, the anchors 22 and extenders 100 are inserted percutaneously without sequential dilation. The guidewire is positioned as discussed above, and anchor 22 can be cannulated for positioning over the guidewire. The respective anchors 22 and extenders 100 are assembled and then positioned together over the guidewire, which guides the anchor to the pedicle or other targeted portion of the vertebra. A cannulated driver tool is positioned over the guidewire and through the extender to engage the head of the anchor and drive it into the vertebra.

In another embodiment, a pathway to the target location is prepared as discussed above. The guidewire and any dilators are removed. A cannula or other suitable retractor may remain in the incision to provide a protected pathway to the target location, although direct insertion through a micro-incision is also contemplated. Anchors 22 are engaged to their respective extender 100, and an anchor driver is inserted through the extender and engaged to the head of the screw portion of the anchor. The anchors 22 and extenders 100 are inserted percutaneously to the target location of the respective vertebra, such as the pedicle. Insertion and alignment of anchors 22 may be monitored fluoroscopically or with any suitable surgical navigation system. The screw portion of the anchor is then engaged to the vertebra at the target location with the extender 100 attached to receiver portion 26 of its respective anchor 22. Anchor and extender insertion and engagement is repeated for each vertebra.

In any embodiment, placement of the anchors 22 and extenders 100 can be conducted through a micro-incision, through a retracted opening formed in the tissue approaching the targeted location on the vertebra, or through a tubular member providing a protected passageway to one or more of the adjacent vertebrae. Furthermore, since connecting member 40 is directed from one anchor to the other below the muscle plane that lies along the spinal column, no incision is required between extenders 100, nor is any entry puncture or incision remote from extenders 100 required.

Once the extenders 100 and anchors 22 are positioned in the patient and secured to the respective bony structures of the spinal column, extenders 100 are oriented so that receptacles 28 in receiver portions 26 of anchors 22 are aligned with one another in a manner that permits connecting member 40 to be advanced from one receptacle 28 to the other in a direction transverse to extenders 100 as shown in FIG. 6. The alignment may be verified and maintained by any one or combination of visual indicators on extenders 100, by imaging techniques, or by securing orientation guide 400 to the proximal ends of extenders 100 as shown in FIG. 11.

Tissue retractor 200 is then positioned through passage 120 of one of the extenders 100 with retracting blade 204 in longitudinal alignment with shaft 202 and extender 100. Handle assembly 206 is then actuated to pivot retracting blade 204 to a transverse orientation to shaft portion 202 and extender 100, such as shown in FIG. 6. During pivoting of retracting blade 204, downward pressure can be applied to shaft portion 204 to move retractor 200 distally in extender 100 so that retracting blade 204 is located as far distally relative to extender 100 as possible. When retracting blade 204 is pivoted to the desired orientation, pinion 252 is rotated to raise retractor 200 and blade 204 proximally away from the vertebrae. Retracting blade 204 lifts the adjacent tissue away from the spine to create a pathway along the spine from the distal end of the extender in which retractor 200 is located toward the other extender.

With the tissue retracted, connecting member 40 is inserted into second passage 150 and guided along extender 100 to receptacle 28 of the anchor 22 to which it is mounted. Connecting member 40 can be engaged at its trailing end with an inserter such as inserter 300 and inserter 300 is used to facilitate placement of connecting member 40 along second passage 150. The ramped surface portion 131 along second passage 150 facilitates guiding connecting member 40 into the receptacle 28 of anchor 22 and in changing the orientation of connecting member 40 from its initial insertion orientation to a second orientation where connecting member 40 is transversely oriented to extender 100. Connecting member 40 is further advanced along the spinal column through the pathway created by retracting blade 204 to the other anchor and extender. When connecting member 40 is positioned to extend between or is aligned with passages 120 of both extenders 100, a set screw or other securing member 38 is positioned through each of the passages 120 and engaged to the respective anchor 22 with a set screw driver or other suitable instrument. If reduction of connecting member 40 into receptacle 28 is required prior to insertion of the engaging member, retractor 200 can be moved distally along the extender 100 in which it located so that retracting blade 204 contacts connecting member 40 and moves it distally toward the receptacles 28 of anchors 22. After connecting member 40 is oriented between the extenders 100 or secured to each of the anchors 22 with a securing member, inserter 300 is detached from connecting member 40 and extenders 100 are detached from anchors 22 to provide the final assembled construct.

It may also be desirable to provide a desired alignment between vertebrae by moving one or more vertebrae to place connecting member 40 into receiver portions 26 of anchors 22. For example, the vertebrae may be misaligned as a result of spondylolisthesis, anatomical differences between the vertebrae, or some other condition. Also, there may be slight misalignments between receiver portions 26 that make manually positioning connecting member 40 into each of the receiver portions difficult. In such situations, a separate reduction instrument can be employed through or around one or more of extenders 100. Alternatively, one of the extenders can be modified to perform the reduction by moving outer member 130 along inner member 110 to contact connecting member 40 and provide a mechanical advantage to seat connecting member 40 in receiver portion 26 of one or more of anchors 22.

While the invention has been illustrated and described in detail in the drawings and foregoing description, the same is to be considered as illustrative and not restrictive in character, and that all changes and modifications that come within the spirit of the invention are desired to be protected.

What is claimed is:

1. A spinal surgical system, comprising:
a first anchor engageable to the spinal column, said first anchor including a bone engaging portion and a receiver portion with a receptacle;
a first extender extending along a longitudinal axis between a proximal end and a distal end, said first extender including an elongated inner member releasably engaged to said receiver portion of said first anchor at said distal end, said inner member including a first passage extending from said proximal end to said receptacle of said receiver portion when said inner member is engaged to said receiver portion, said first extender further including an elongated outer member having an inner surface positioned around an outer surface of said inner member, wherein said inner surface of said outer member and said outer surface of said inner member each include a recessed portion therein that together define a second passage between said inner member and said outer member when said recessed portions are aligned that extends along said first extender and opens at said proximal end of said first extender and opens into said receptacle of said receiver portion, said second passage being separate and distinct from said first passage;
a second anchor engageable to the spinal column, said second anchor including a bone engaging portion and a receiver portion with a receptacle;
a second extender extending along a longitudinal axis between a proximal end and a distal end, said distal end being releasably engageable to said second anchor; and
a connecting member having a length sized to extend between said receiver portions of said first and second anchors when said first and second anchors are engaged to the spinal column, wherein said second passage is sized to receive said connecting member therein so that said connecting member is maneuverable through said second passage from said proximal end of said first extender toward said receiver portion of said first anchor and then from said first extender toward said receiver portion of said second anchor so that said connecting member is positioned to extend between said receptacles of said first and second anchors.

2. The system of claim 1, wherein said recessed portion of said outer member includes a ramped surface portion that begins at a location proximal of a distal end of said outer member of said first extender and slopes from said location toward said inner member to said distal end of said outer member.

3. The system of claim 1, wherein said inner member includes a tubular body portion extending distally from said proximal end of said first extender and said inner member includes a pair of arms extending distally from said tubular body portion to said distal end of said first extender, said pair of arms being separated from one another by a slot therebetween, wherein said recessed portion of said inner member extends from said proximal end to said slot.

4. The system of claim 1, further comprising a retractor, said retractor including a shaft positioned in said first passage and a retracting blade at a distal end of said shaft, said retracting blade extending transversely to said shaft and projecting outwardly from said first extender adjacent said distal end of said first extender toward said second extender.

5. The system of claim 4, wherein said inner member includes a tubular body portion extending distally from said proximal end and a pair of arms extending distally from said tubular body portion to said distal end of said first extender, said pair of arms being separated from one another by a slot therebetween, wherein said outer member includes a notch extending from a distal end of said outer member toward said proximal end of said extender, said notch being located on a side of said first extender opposite said second passage and said retracting blade extends through said notch.

6. The system of claim 4, wherein said first extender includes a pinion mounted thereto that extends into said first passage and said shaft of said retractor includes a ratchet surface engaged to said pinion, said pinion being movable to move said shaft in said first extender to adjust a position of said retracting blade relative to said distal end of said first extender.

7. The system of claim 1, further comprising an orientation guide including first and second mounting portions mounted to said proximal ends of respective ones of said first and second extenders, said first and second mounting portions being adjustably connected to one another to vary a spacing therebetween to adapt to a distance between said proximal ends of said first and second extenders, said orientation guide engaging said first and second extenders so that said receptacles of said first and second anchors are aligned with one another to receive said connecting member therebetween.

8. The system of claim 1, wherein said first and second mounting portions are angled relative to one another to accommodate a non-parallel relationship between said first and second extenders.

9. A surgical system comprising:
a first anchor engageable to the spinal column, said first anchor including a bone engaging portion and a receiver portion with a receptacle;
a first extender extending along a longitudinal axis between a proximal end and a distal end, said first extender including an elongated inner member with first and second arms releasably engaged to said receiver portion of said first anchor at said distal end, said inner member including a first passage extending from said proximal end to said receptacle of said receiver portion when said inner member is engaged to said receiver portion, said first extender further including an elongated outer member having an inner surface positioned around an outer surface of said inner member, wherein said inner surface of said outer member and said outer surface of said inner member each include a recessed portion therein that together define a second passage between said outer surface of said inner member and said inner surface of said outer member when said recessed portions are aligned, wherein said second passage extends along said first extender from a proximal opening of said second passage at said proximal end of said first extender to a distal opening of said second passage between said arms of said inner member, and wherein said second passage is separate and distinct from said first passage;
a second anchor engageable to the spinal column, said second anchor including a bone engaging portion and a receiver portion with a receptacle;
a second extender extending along a longitudinal axis between a proximal end and a distal end, said distal end being releasably engageable to said second anchor; and
a connecting member having a length sized to extend between said receiver portions of said first and second anchors when said first and second anchors are engaged to the spinal column, where said second passage is sized to receive said connecting member therein so that said connecting member is maneuverable through said second passage from said proximal end of said first extender toward said receiver portion of said first anchor and then from said first extender toward said receiver portion of said second anchor so that said connecting member is positioned to extend between said receptacles of said first and second anchors.

10. The system of claim 9, wherein said recessed portion of said outer member includes a ramped surface portion that begins at a location proximal of a distal end of said outer member of said first extender and slopes from said location toward said inner member to said distal end of said outer member.

11. The system of claim 9, wherein said inner member includes a tubular body portion extending distally from said proximal end of said first extender and said pair of arms of said inner member extend distally from said tubular body portion to said distal end of said first extender, said pair of arms being separated from one another by a slot therebetween, wherein said recessed portion of said inner member extends from said proximal end to said slot.

12. The system of claim 9, further comprising an orientation guide including first and second mounting portions mounted to said proximal ends of respective ones of said first and second extenders, said first and second mounting portions being adjustably connected to one another to vary a spacing therebetween to adapt to a distance between said proximal ends of said first and second extenders, said orientation guide engaging said first and second extenders so that said receptacles of said first and second anchors are aligned with one another to receive said connecting member therebetween.

13. The system of claim 12, wherein said first and second mounting portions are angled relative to one another to accommodate a non-parallel relationship between said first and second extenders.

14. A spinal surgical system, comprising:
a first anchor engageable to the spinal column, said first anchor including a bone engaging portion and a receiver portion with a receptacle;
a first extender extending along a longitudinal axis between a proximal end and a distal end, said first extender including an elongated inner member releasably engaged to said receiver portion of said first anchor at said distal end, said inner member including a first passage extending from said proximal end to said receptacle of said receiver portion when said inner member is engaged to said receive portion, said first extender further including an elongated outer member having an inner surface positioned around an outer surface of said inner member, wherein said outer member and said inner member each include a recessed portion together defining a second passage between said inner member and said outer member when said recessed portions are aligned, said second passage extending along said first extender from said proximal end of said first extender to said receptacle of said receiver portion and being separate and distinct from said first passage;
a second anchor engageable to the spinal column, said second anchor including a bone engaging portion and a receiver portion with a receptacle;
a second extender extending along a longitudinal axis between a proximal end and a distal end, said distal end being releasably engageable to said second anchor;
a connecting member having a length sized to extend between said receiver portions of said first and second anchors when said first and second anchors are engaged to the spinal column, wherein said second passage is sized to receive said connecting member therein so that said connecting member is maneuverable through said second passage from said proximal end of said first extender toward said receiver portion of said first anchor and then from said first extender toward said receiver portion of said second anchor so that said connecting member is positioned to extend between said receptacles of said first and second anchors; and
a retractor, said retractor including a shaft positioned in said first passage and a retracting blade at a distal end of said shaft, said retracting blade extending transversely to said shaft and projecting outwardly from said first passage of said first extender at a location adjacent to said distal end of said first extender to project from said first extender toward said second extender.

15. The system of claim 14, wherein said inner member includes a tubular body portion extending distally from said proximal end and a pair of arms extending distally from said tubular body portion to said distal end of said first extender, said pair of arms being separated from one another by a slot therebetween, wherein said outer member includes a notch extending from a distal end of said outer member toward said proximal end of said extender, said notch being located on a side of said first extender opposite said second passage and said retracting blade extends through said notch.

16. The system of claim 14, wherein said first extender includes a pinion mounted thereto that extends into said passage and said shaft of said retractor includes a ratchet surface engaged to said pinion, said pinion being movable to move said shaft in said first extender to adjust a position of said retracting blade relative to said distal end of said first extender.

* * * * *